(12) United States Patent
Sato et al.

(10) Patent No.: US 6,476,221 B1
(45) Date of Patent: Nov. 5, 2002

(54) TRIBENZAZEPINE COMPOUND AND PRODUCTION METHOD THEREOF

(75) Inventors: Tadahisa Sato, Kanagawa (JP); Masuji Motoki, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/672,991

(22) Filed: Sep. 29, 2000

(30) Foreign Application Priority Data

Sep. 29, 1999 (JP) .......................................... 11-277015

(51) Int. Cl.[7] .............................................. C07D 223/14
(52) U.S. Cl. ...................................................... 540/576
(58) Field of Search .......................................... 540/576

(56) References Cited

FOREIGN PATENT DOCUMENTS

JP         A-10-59943         3/1998

OTHER PUBLICATIONS

J. Org. Chem., 56, 3906–3908 (1991).

*Primary Examiner*—Brenda Coleman
(74) *Attorney, Agent, or Firm*—Sughrue Mion, PLLC

(57) ABSTRACT

This invention provides a compound which is useful as an electric charge transportation agent for electrophotographic photosensitive materials and organic EL devices, and its production method. Illustratively, a compound of formula (I) is produced by way of a dehydration reaction of a compound of formula (II).

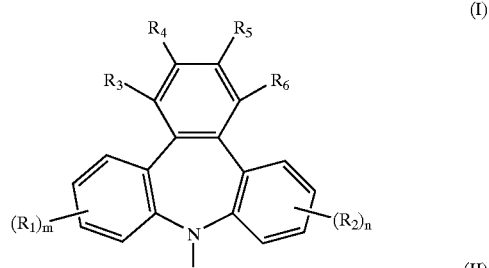

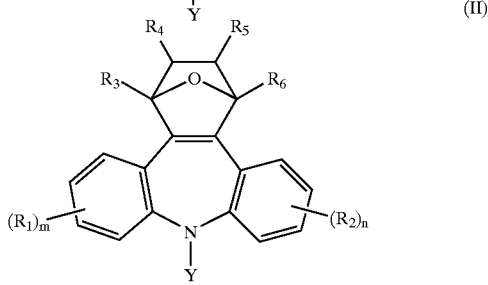

17 Claims, No Drawings

TRIBENZAZEPINE COMPOUND AND PRODUCTION METHOD THEREOF

FIELD OF THE INVENTION

This invention relates to a method for the production of tribenzazepine compounds which are useful as the synthesis material of electric charge transportation agents to be used, e.g., in photosensitive materials for electrophotography use and organic electroluminescence (EL) devices.

DESCRIPTION OF THE RELATED ART

In recent years, organic substances are mainly used as the photoconductive material of photosensitive materials to be used in the electrophotographic system. Their examples include a photosensitive material comprised of poly-N-vinylcarbazole and 2,4,7-trinitrofluoren-9-one (U.S. Pat. No. 3,484,237), a material in which poly-N-vinylcarbazole is sensitized with a pyrylium salt based pigment (JP-B-48-25658; the term "JP-B" as used herein means an "examined Japanese patent publication"), a photosensitive material which contains an organic pigment as the main component (JP-A-47-37543; the term "JP-A" as used herein means an "unexamined published Japanese patent application"), a photosensitive material which contains a euteric complex comprised of a dyestuff and a resin as the main component (JP-A-47-10735), a photosensitive material which contains a hydrazone based compound as the main component (JP-A-57-101844 and JP-A-54-150128), a photosensitive material which contains an aromatic tertiary amine based compound as the main component (JP-B-58-32372) and a photosensitive material which contains a stilbene based compound as the main component (JP-A-58-198043). These photosensitive materials seem to have high practical values because of their excellent characteristics, but when various requirements for photosensitive materials to be used in the electrophotographic system are taken into consideration, it is the actual circumstances that a material which fully satisfies these requirements is not available yet. Accordingly, studies are still being carried out actively on the photosensitive materials for electrophotography use in which organic substances, particularly organic electric charge transportation agents, are used.

VanSlyke and Tang et al. have revealed that, when an aromatic tertiary amine containing phenyl, phenylene or biphenylene group is used as an electric charge transportation agent in the positive hole injection/transportation region of an internally connected organic EL apparatus, stability of the optical output is improved and the operating life is thereby prolonged, as they have disclosed for example in U.S. Pat. Nos. 4,539,507 and 4,720,432 and JP-A-5-234,681. Thereafter, in order to obtain more stable optical output, attempts have been made by many researchers to improve aromatic tertiary amine based electric charge transportation agents to be used in the positive hole injection transportation region, and the results have been reported in a large number of patent applications and scientific papers. Examples of these reports include *Japanese Journal of Applied Physics*, 27, L269 (1988), JP-A-59-194393, *Appl. Phys. Lett.*, 66,2679 (1995), JP-A-5-234681, JP-A-7-331238, JP-A-8-48656 and WO 95/09147 regarding biphenyl based tertiary amines and *Appl. Phys. Lett.*, 65, 807 (1994) and JP-B-7-110940 regarding star burst tertiary amines. However, since these amines are still insufficient for practical use, such studies are conducted more actively by a large number of researchers.

It has been disclosed recently that a compound having tribenzazepine structure in its molecule is useful as an electric charge transportation agent of electrophotography and organic EL device (JP-A-10-59943, JP-A-10-219241, JP-A-10-316875, JP-A-10-324680 and JP-A-10-330365). However, the tribenzazepine synthesis methods so far known were difficult to be applied to the industrial large scale synthesis because of the use of deoxidation reaction by a special reagent (*J. Org. Chem.*, 56, 3906 (1991)).

SUMMARY OF THE INVENTION

In view of the above, it therefore becomes an object of the invention to provide a new method for the synthesis of tribenzazepine compounds which are useful as the synthesis material of electric charge transportation agents to be used, e.g., in photosensitive materials for electrophotography use and organic electric field generation devices.

As a result of intensive studies, the present inventors have found a tribenzazepine structure synthesizing method which does not use a special reagent and accomplished the invention based on this finding.

Accordingly, the invention provides (1) a method for the production of a tribenzazepine compound represented by formula (I), which comprises carrying out the process by way of a dehydration reaction of a compound represented by formula (II):

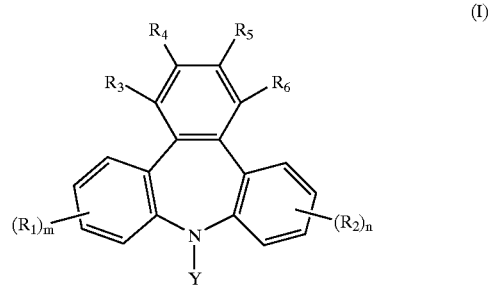

wherein Y represents a hydrogen atom or an alkyl, aryl, acyl, alkoxycarbonyl, aryloxycarbonyl, alkanesulfonyl or arenesulfonyl group, each of $R_1$ and $R_2$ represents a hydrogen or halogen atom or an alkyl, aryl, hydroxy, alkoxy, aryloxy, acyl, alkoxycarbonyl, aryloxycarbonyl, formyl, carboxyl, sulfo or amino group, each of $R_3$, $R_4$, $R_5$ and $R_6$ represents a hydrogen atom or an alkyl or aryl group, and each of m and n is an integer of from 1 to 4.

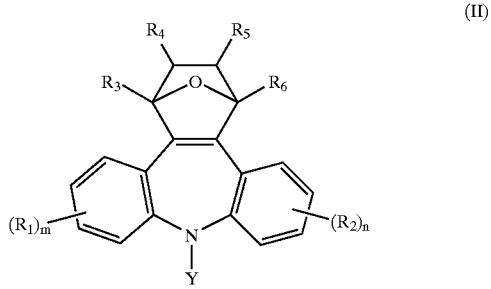

wherein Y, $R_1$, $R_2$, $R_3$, $R_4$, $R_5$, $R_6$, m and n are as defined in the above, (2) a method for the production of a compound represented by formula (I) described in the above item (1), wherein the compound represented by formula (II) is produced by reducing a compound. represented by formula (III):

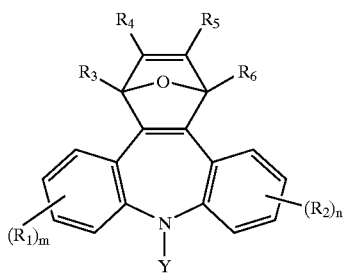

(III)

wherein Y, $R_1$, $R_2$, $R_3$, $R_4$, $R_5$, $R_6$, m and n are as defined in the foregoing, and (3) a tribenzazepine compound represented by formula (IV):

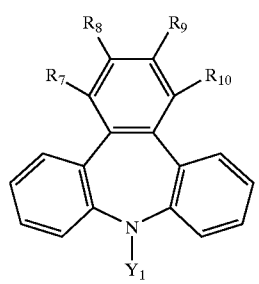

(IV)

wherein $Y_1$ represents a group having the same meaning of the Y, and each of $R_7$, $R_8$, $R_9$, and $R_{10}$ represents a hydrogen atom or an alkyl group having 10 or less of carbon atoms, with the proviso that all of $R_7$ to $R_{10}$ are not hydrogen atoms at the same time and that $Y_1$ does not represent hydrogen atom or an aryl group when $R_8$ is methyl group and each of $R_7$, $R_9$ and $R_{10}$ is hydrogen atom.

In this connection, according to the invention, it is intended that the respective groups represented by Y, $R_1$, $R_2$, $R_3$, $R_4$, $R_5$ and $R_6$ in the formulae (I) to (III) include not only unsubstituted groups but also those which are further substituted with substituent groups as is evident from the following descriptions.

Other objects and advantages of the invention will be made apparent as the description progresses.

DETAILED DESCRIPTION OF THE INVENTION

Firstly, Y, $Y_1$, $R_1$, $R_2$, $R_3$, $R_4$, $R_5$, $R_6$, $R_7$, $R_8$, $R_9$, $R_{10}$, m and n in the formulae (I) to (IV) are described.

Each of Y and $Y_1$ represents a hydrogen atom or an alkyl, aryl, acyl, alkoxycarbonyl, aryloxycarbonyl, alkanesulfonyl or arenesulfonyl group, and more detailed examples of the groups excluding hydrogen atom, in the case of unsubstituted groups, are an alkyl group having from 1 to 20 carbon atoms, an aryl group having from 6 to 36 carbon atoms, an acyl group having from 2 to 20 carbon atoms, an alkoxycarbonyl group having from 2 to 20 carbon atoms, an aryloxycarbonyl group having from 7 to 40 carbon atoms, an alkanesulfonyl group having from 1 to 20 carbon atoms and an arenesulfonyl group having from 6 to 40 carbon atoms.

Their illustrative examples include an alkyl group such as methyl, ethyl, isopropyl, n-butyl, t-butyl, n-dodecyl or cyclohexyl, an aryl group such as phenyl, naphthyl, anthracenyl, phenanthrenyl, pyrenyl, naphthacenyl, pentacenyl or pentaphenyl, an acyl group such as acetyl, propionyl or benzoyl, an alkoxycarbonyl group such as methoxycarbonyl, ethoxycarbonyl or octyloxycarbonyl, an aryloxycarbonyl group such as phenoxycarbonyl or 2-naphthyloxycarbonyl, an alkanesulfonyl group such as methanesulfonyl or ethanesulfonyl and an arenesulfonyl group such as benzenesulfonyl, p-toluenesulfonyl or 2-naphthalenesulfonyl.

Preferred among them is hydrogen atom, an alkyl, an aryl group, an acyl or alkoxycarbonyl group, and particularly preferred is hydrogen atom, an acyl group or an alkoxycarbonyl group.

Each of $R_1$ and $R_2$ represents a hydrogen or halogen atom, a substituted or unsubstituted alkyl, aryl, alkoxy, aryloxy or acyl group or a formyl, carboxyl, sulfo or amino group, and more detailed examples of the groups excluding hydrogen atom and the formyl, carboxyl, sulfo and amino groups, are a halogen atom such as fluorine, chlorine or bromine and, in the case of unsubstituted groups, an alkyl group having from 1 to 20 carbon atoms, an aryl group having from 6 to 36 carbon atoms, an alkoxy group having from 1 to 20 carbon atoms, an aryloxy group having from 6 to 36 carbon atoms, an acyl group having from 2 to 20 carbon atoms, an alkoxycarbonyl group having from 2 to 20 carbon atoms and an aryloxycarbonyl group having from 7 to 40 carbon atoms.

Their illustrative examples excluding halogen atoms include an alkyl group such as methyl, ethyl, isopropyl, n-butyl, t-butyl, n-dodecyl or cyclohexyl, an aryl group such as phenyl, naphthyl, anthracenyl, phenanthrenyl, pyrenyl, naphthacenyl, pentacenyl or pentaphenyl, an alkoxyl group such as methoxy, ethoxy, isopropoxy, n-hexyloxy, cyclohexyloxy, octyloxy or dodecyloxy, an aryloxy group such as phenoxy, naphthoxy, anthracenoxy or pentacenoxy, an acyl group such as acetyl, propionyl or benzoyl, an alkoxycarbonyl group such as methoxycarbonyl, ethoxycarbonyl or octyloxycarbonyl and an aryloxycarbonyl group such as phenoxycarbonyl or 2-naphthyloxycarbonyl.

When these groups have substituent groups, examples of such substituent groups include a halogen atom and an alkyl, aryl, heterocyclic, cyano, hydroxy, nitro, carboxy, sulfo, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyloxy, aryloxycarbonylamino, imido, heterocyclic thio, sulfinyl, phosphonyl, aryloxycarbonyl, acyl, silyl or azolyl group.

Regarding $R_1$ and $R_2$, hydrogen atom, an alkyl group, an aryl group or an alkoxy group is preferable, and hydrogen atom is particularly preferable.

Each of $R_3$ to $R_6$ represents a hydrogen atom or an alkyl or aryl group, illustratively, the same group as defined in $R_1$ and $R_2$. Preferably, each of $R_3$ to $R_6$ is hydrogen atom or an alkyl group. Particularly preferred is hydrogen atom or methyl group.

Each of $R_7$, $R_8$, $R_9$, and $R_{10}$ represents hydrogen atom or an alkyl group having 10 or less of carbon atoms with the proviso that all of $R_7$ to $R_{10}$ are not hydrogen atoms at the same time. Preferably $R_7$ to $R_{10}$ are each hydrogen atom or an unsubstituted alkyl group, and one of them is an unsubstituted alkyl group. Illustrative examples of the unsubstituted alkyl group include an alkyl group such as methyl, ethyl, n-propyl, n-butyl, n-octyl, n-dodecyl, isopropyl, t-butyl, 2-ethylhexyl or cyclohexyl. Preferred is methyl, ethyl or isopropyl.

When $R_8$ is methyl group and each of $R_7$, $R_9$ and $R_{10}$ is hydrogen atom, $Y_1$ represents a group other than hydrogen atom or an aryl group, but preferably, $Y_1$ is an alkyl, acyl or alkoxycarbonyl group.

Each of m and n is an integer of from 1 to 4, preferably 1.

Next, illustrative examples of the compounds of the invention represented by the formulae (I), (II), (III) and (IV) are shown in Tables 1, 2, 3 and 4, though the invention is not limited thereto.

TABLE 1

Formula (I)

| No. | R₁ | R₂ | R₃ | R₄ | R₅ | R₆ | Y | m | n |
|---|---|---|---|---|---|---|---|---|---|
| I-1 | H | H | H | H | H | H | H | 1 | 1 |
| I-2 | H | H | H | H | H | H | CH$_3$CO— | 1 | 1 |
| I-3 | H | H | H | H | H | H | C$_2$H$_5$OCO— | 1 | 1 |
| I-4 | H | H | H | H | H | H | CH$_3$— | 1 | 1 |
| I-5 | H | H | H | H | H | H | CH$_3$SO$_2$— | 1 | 1 |
| I-6 | H | H | H | H | H | H | C$_6$H$_5$SO$_2$— | 1 | 1 |
| I-7 | H | H | H | H | H | H | C$_6$H$_5$— | 1 | 1 |
| I-8 | H | H | CH$_3$ | H | H | H | H | 1 | 1 |
| I-9 | H | H | CH$_3$ | H | H | H | CH$_3$CO— | 1 | 1 |
| I-10 | H | H | H | CH$_3$ | H | H | H | 1 | 1 |
| I-11 | H | H | H | CH$_3$ | H | H | CH$_3$CO— | 1 | 1 |
| I-12 | 3-NH$_2$ | H | H | H | H | H | p-NH$_2$C$_6$H$_4$— | 1 | 1 |
| I-13 | 3-Cl | 7-Cl | H | H | H | H | H | 1 | 1 |
| I-14 | 2-CH$_3$ | 7-C$_6$H$_5$— | H | H | H | H | H | 1 | 1 |
| I-15 | 1-COOH | 5-CH$_3$O— | H | H | H | H | H | 1 | 1 |
| I-16 | 3-SO$_3$H | H | H | H | H | H | C$_6$H$_5$CO— | 1 | 1 |
| I-17 | 2-CH$_3$, 3-Cl | H | H | H | H | H | H | 2 | 1 |

TABLE 2

Formula (II)

| No. | R₁ | R₂ | R₃ | R₄ | R₅ | R₆ | Y | m | n |
|---|---|---|---|---|---|---|---|---|---|
| II-1 | H | H | H | H | H | H | H | 1 | 1 |
| II-2 | H | H | H | H | H | H | CH$_3$CO— | 1 | 1 |
| II-3 | H | H | H | H | H | H | C$_2$H$_5$OCO— | 1 | 1 |
| II-4 | H | H | H | H | H | H | CH$_3$— | 1 | 1 |
| II-5 | H | H | H | H | H | H | CH$_3$SO$_2$— | 1 | 1 |
| II-6 | H | H | H | H | H | H | C$_6$H$_5$SO$_2$— | 1 | 1 |
| II-7 | H | H | H | H | H | H | C$_6$H$_5$— | 1 | 1 |
| II-8 | H | H | CH$_3$ | H | H | H | H | 1 | 1 |
| II-9 | H | H | CH$_3$ | H | H | H | CH$_3$CO— | 1 | 1 |
| II-10 | H | H | H | CH$_3$ | H | H | H | 1 | 1 |
| II-11 | H | H | H | CH$_3$ | H | H | CH$_3$CO— | 1 | 1 |
| II-12 | 3-NH$_2$ | H | H | H | H | H | p-NH$_2$C$_6$H$_4$— | 1 | 1 |
| II-13 | 3-Cl | 7-Cl | H | H | H | H | t-C$_4$H$_9$OCO— | 1 | 1 |
| II-14 | 2-CH$_3$ | 7-C$_6$H$_5$— | H | H | H | H | H | 1 | 1 |
| II-15 | 1-COOC$_2$H$_5$ | 5-CH$_3$O— | H | H | H | H | H | 1 | 1 |
| II-16 | 3-SO$_3$H | H | H | H | H | H | C$_6$H$_5$CO— | 1 | 1 |
| II-17 | 2-CH$_3$, 3-Cl | H | H | H | H | H | H | 2 | 1 |

TABLE 3

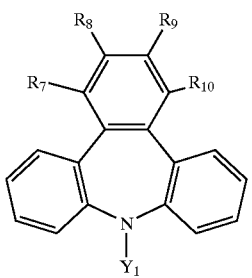

Formula (III)

| No. | $R_1$ | $R_2$ | $R_3$ | $R_4$ | $R_5$ | $R_6$ | Y | m | n |
|---|---|---|---|---|---|---|---|---|---|
| III-1 | H | H | H | H | H | H | H | 1 | 1 |
| III-2 | H | H | H | H | H | H | $CH_3CO-$ | 1 | 1 |
| III-3 | H | H | H | H | H | H | $C_2H_5OCO-$ | 1 | 1 |
| III-4 | H | H | H | H | H | H | $CH_3-$ | 1 | 1 |
| III-5 | H | H | H | H | H | H | $CH_3SO_2-$ | 1 | 1 |
| III-6 | H | H | H | H | H | H | $C_6H_5SO_2-$ | 1 | 1 |
| III-7 | H | H | H | H | H | H | $C_6H_5-$ | 1 | 1 |
| III-8 | H | H | $CH_3$ | H | H | H | H | 1 | 1 |
| III-9 | H | H | $CH_3$ | H | H | H | $CH_3CO-$ | 1 | 1 |
| III-10 | H | H | H | $CH_3$ | H | H | H | 1 | 1 |
| III-11 | H | H | H | $CH_3$ | H | H | $CH_3CO-$ | 1 | 1 |
| III-12 | $3-NO_2$ | H | H | H | H | H | $p-NO_2C_6H_4-$ | 1 | 1 |
| III-13 | 3-Cl | 7-Cl | H | H | H | H | $t-C_4H_9OCO-$ | 1 | 1 |
| III-14 | $2-CH_3$ | $7-C_6H_5-$ | H | H | H | H | $C_6H_5CH_2OCO-$ | 1 | 1 |
| III-15 | $1-COOC_2H_5$ | $5-CH_3O-$ | H | H | H | H | H | 1 | 1 |
| III-16 | $3-SO_3H$ | 7-I | H | H | H | H | $C_6H_5CO-$ | 1 | 1 |
| III-17 | $2-CH_3$, 3-Cl | H | H | H | H | H | H | 2 | 1 |

TABLE 4

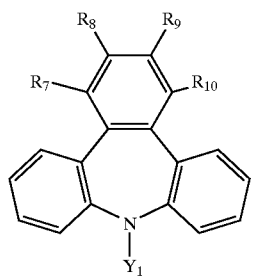

Formula (IV)

| No. | $R_7$ | $R_8$ | $R_9$ | $R_{10}$ | $Y_1$ | Remarks |
|---|---|---|---|---|---|---|
| IV-1 | H | $CH_3$ | H | H | $-COOC_2H_5$ | |
| IV-2 | $CH_3$ | H | H | H | H | Identical to the example compound (I-8) |
| IV-3 | $CH_3$ | H | H | H | $-COCH_3$ | Identical to the example compound (I-9) |
| IV-4 | $CH_3$ | $CH_3$ | H | H | H | |
| IV-5 | $C_2H_5$ | H | H | H | H | |
| IV-6 | $i-C_3H_7$ | H | H | H | H | |
| IV-7 | H | $CH_3$ | H | H | $C_2H_5$ | |
| IV-8 | H | $CH_3$ | H | H | $-COCH_3$ | Identical to the example compound (I-11) |
| IV-9 | H | $CH_3$ | $CH_3$ | H | H | |
| IV-10 | $CH_3$ | H | H | $CH_3$ | H | |
| IV-11 | H | $t-C_4H_9$ | H | H | H | |
| IV-12 | H | $c-C_6H_{11}$ | H | H | H | |
| IV-13 | $CH_3$ | H | H | H | $C_6H_5$ | |
| IV-14 | $CH_3$ | H | H | H | $CH_3$ | |
| IV-15 | H | $CH_3$ | H | H | $-SO_2CH_3$ | |
| IV-16 | H | $C_6H_5$ | H | H | H | |

Next, the production method of the invention is described in the following. A scheme of the production method is shown below.

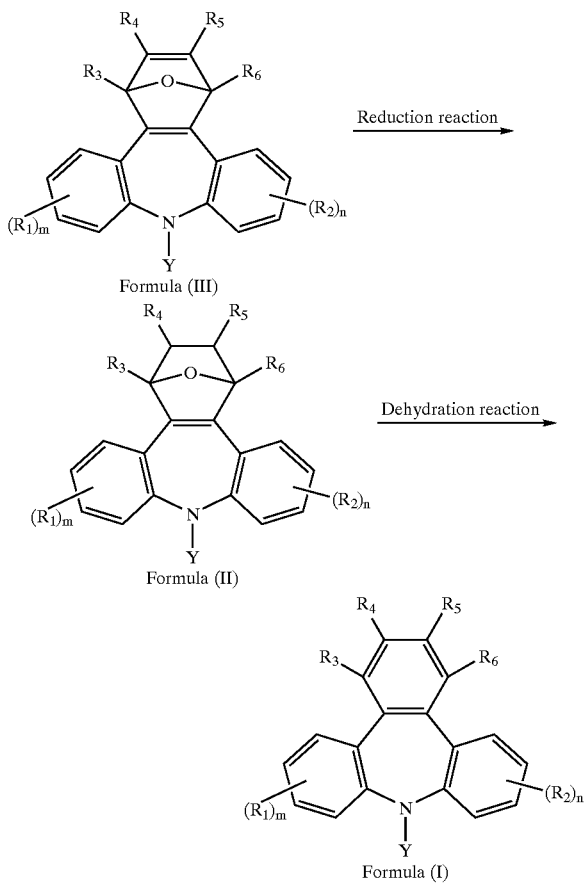

Formula (III)

Formula (II)

Formula (I)

In the above formulae, Y, $R_1$, $R_2$, $R_3$, $R_4$, $R_5$, $R_6$, m and n are as defined in the foregoing.)

The compound of formula (III) shown in the scheme can be produced using the method described in *J. Org. Chem.*, 56, 3906 (1991). That is, it can be produced by allowing a 1-O-bromo-5H-dibenz[b,f]azepine compound to react with a furan compound in the presence of a strong base.

In illustratively describing, the reduction method from the formula (III) to the formula (II) of the invention is a reduction reaction which uses hydrogen and a catalyst (generally called "catalytic reduction reaction") or a reduction method which uses, e. g., a diimide reduction reaction. Examples of the catalyst to be used in the catalytic reduction reaction include a heterogeneous catalyst such as Raney nickel or palladium-carbon and a homogeneous catalyst such as chlorotris(triphenylphosphine)rhodium (I). According to the diimide reduction, examples of the method for generating diimide include a method in which decomposition of an azodicarboxylate is carried out and a method in which elimination reaction from N-arenesulfonylhydrazide or N-acylhydrazine is carried out. Preferred reduction method is a method in which catalytic reduction reaction is carried out using a heterogeneous catalyst.

Examples of the solvent tribe used in the reduction reaction include an alcohol solvent such as methanol or isopropanol, an ester solvent such as ethyl acetate, an amide solvent such as N,N-dimethylformamide or N,N-dimethylacetamide, an ether solvent such as tetrahydrofuran or dimethoxyethane, a hydrocarbon organic solvent such as hexane or toluene and an organic acid solvent such as acetic acid, which may be used alone or as a mixture. When the substrate is soluble in water, water can also be used as a solvent. Amount of the solvent is from 1 to 20 parts by weight, preferably from 5 to 10 parts by weight, based on 1 part by weight of the substrate.

Reaction temperature for the reduction is from −20 to 100° C., preferably from 10 to 60° C. The reaction period is from 0.5 to 10 hours, preferably from 1 to 5 hours. In the case of the catalytic reduction method, the pressure of hydrogen is from ordinary pressure to 100 kg/cm², preferably from 5 to 50 kg/cm².

In the case of the catalytic reduction method, amount of the catalyst is from 0.001 to 20 mol %, preferably from 0.1 to 10 mol %, based on the substrate. In the case of the diimide reduction method, amount of the diimide to be used is from 1 to 10 equivalents, preferably from 1.2 to 5 equivalents, based on the substrate.

Next, the dehydration reaction from formula (II) to formula (I) is described in detail. The dehydration reaction is generally carried out by heating in the presence an acid catalyst. The acid to be used is sulfuric acid, phosphoric acid, an alkanesulfonic acid, an arenesulfonic acid, a Lewis acid, activated clay or a solid acid, of which an alkanesulfonic acid or an arenesulfonic acid is preferable. Particularly preferred is an arenesulfonic acid, and its illustrative examples include benzenesulfonic acid and p-benzenesulfonic acid. Amount of the catalyst to be used is from 0.1 to 2 equivalents, preferably from 0.2 to 10 equivalent, based on the substrate.

Examples of the reaction solvent to be used include an alcohol solvent such as methanol or isopropanol, an ester solvent such as ethyl acetate, an amide solvent such as N,N-dimethylformamide or N,N-dimethylacetamide, an aliphatic hydrocarbon solvent such as hexane or heptane, an aromatic hydrocarbon solvent such as benzene, toluene or chlorobenzene and an organic acid solvent such as acetic acid, of which an aliphatic hydrocarbon or aromatic hydrocarbon organic solvent is preferable. Particularly preferred is an aromatic hydrocarbon organic solvent. Amount of the organic solvent to be used is from 1 to 20 parts by weight, preferably from 2 to 5 parts by weight, based on 1 part by weight of the substrate.

The reaction temperature is from 50 to 200° C., preferably from 60 to 150° C. The reaction period is from 1 to 20 hours, preferably from 3 to 6 hours.

EXAMPLES

The following illustratively describes the invention based on examples, but the invention is not restricted by these examples.

Example 1

(Synthesis of (I-2) and (I-1) from the Example Compound (III-2) by Way of (II-2))

A 10 g (31.8 mmol) portion of 5-acetyl-10-bromo-5H-dibenz[b,f]azepine (*J. Org. Chem.*, 56, 3906 (1991)) was added to 30 ml of t-butanol and stirred at room temperature. To this was added 4.7 g (41.9 mmol) of potassium t-butoxide in portions. To this was then added dropwise 70 ml (954 mmol) of furan spending 5 minutes. Thereafter, this was stirred under heating for about 17 hours and then the solvent was evaporated under a reduced pressure. The resulting residue was mixed with 200 ml of chloroform and water and put into a separating funnel, and the chloroform layer was washed twice with water. This was dried on anhydrous sodium sulfate and then filtered, and the filtrate was concentrated under a reduced pressure to effect precipitation of crystals. The resulting residue was mixed with 30 ml of ethyl acetate, stirred at room temperature for 10 minutes, filtered and then dried to obtain 4.3 g of the example compound (III-2). Yield, 44.5%.

A 3.7 g (12.3 mmol) portion of the example compound (III-2) and 300 ml of methanol were put into an autoclave reaction apparatus, mixed with 0.5 g of 10% palladium-carbon and then stirred at 50° C. for 4 hours under a hydrogen pressure of 59 kg/cm$^2$. This was cooled and allowed to stand overnight, and the thus precipitated crystals were dissolved by adding 10 ml of chloroform and subjected to celite filtration. By concentrating the resulting filtrate under a reduced pressure, crude product of the example compound (II-2) was obtained. This was mixed with 40 ml of toluene and then with p-toluenesulfonic acid monohydrate, and the mixture was heated under reflux for 4 hours while carrying out azeotropic dehydration using a Dean-Stark apparatus. After cooling, this was washed with water, dried and then filtered, and the resulting filtrate was concentrated under a reduced pressure to obtain crude product of the example compound (I-2).

A 480 mg portion of lithium aluminum hydride (LiAlH$_4$) was added to 6 ml of tetrahydrofuran (THF) and stirred for about 10 minutes, and then to this was added dropwise the crude product of the example compound (I-2) which had been dissolved in 5 ml of THF. After about 1 hour of stirring under ice-cooling, to this were added dropwise ethyl acetate and water in that order, and the mixture was filtered through celite and then subjected to separation of layers. After drying, this was filtered and concentrated under a reduced pressure to obtain crystals which were subsequently dissolved in 10 ml of ethyl acetate under heating and then recrystallized by adding 10 ml of n-hexane. After 30 minutes of stirring at room temperature, the suspension was filtered and the resulting crystals were washed with an ethyl acetate/n-hexane (1:1) mixed solvent and dried to obtain 1.81 g (60.5% in yield) of the example compound (I-1). Melting point, 216–218° C. (value in the literature, 220° C.)

NMR (CDCl$_3$, 300 MHz); δ (ppm) 5.20 (1 H, s), 6.90 (2 H, d, J=7.6), 7.15 (2 H, dd), 7.20 (2 H, dd), 7.35–7.60 (6 H, m)

Example 2

(Synthesis of (I-9) and (I-8) from the Example Compound (III-9) by Way of (II-9))

Synthesis of (I-9) from 5-acetyl-10-bromo-5H-dibenz[b,f]azepine by way of the example compounds (III-9) and (II-9) was carried out in almost the same manner as described in Example 1, except that furan was replaced by 2-methylfuran (*Organic Synthesis*, 39, 46 (1959)). Yield of the example compound (III-9) from 5-acetyl-10-bromo-5H-dibenz[b,f]azepine was 50%. Yield of (II-9) from the example compound (III-9) was quantitative, and yield of (I-9) from the example compound (II-9) was 90%. Synthesis of (I-8) from the example compound (I-9) was carried out in the following manner.

A 13.5 g (45 mmol) portion of the example compound (I-9) was dissolved in 400 ml of THF, and 7.6 g (67.5 mmol) of t-BuOK and 0.7 ml of water were added to the solution. After about 1.5 hours of heating under reflux and subsequent evaporation of THF under a reduced pressure, the resulting residue was mixed with ethyl acetate to carry out extraction. After drying and subsequent filtration, the filtrate was concentrated under a reduced pressure, the resulting residue was dissolved in chloroform and passed through a short SiO$_2$ column (eluting solution; chloroform) and then the crystals obtained by concentrating the resulting eluate were recrystallized from a methanol/water system to obtain 10.3 g of the example compound (I-8). Yield, 89%. Melting point, 124 to 125° C.

NMR (CDCl$_3$, 200 MHz); δ (ppm) 2.40 (3 H, s), 5.10 (1 H, brs), 6.8–7.4 (10 H), 7.55 (1 H, d, J=8)

Example 3

(Synthesis of (I-11) and (I-10) from the Example Compound (III-11) by Way of (II-11))

Synthesis of (I-11) and (I-10) from 5-acetyl-10-bromo-5H-dibenz[b,f]azepine by way of the example compounds (III-11) and (II-11) was carried out in almost the same manner as described in Example 1, except that furan was replaced by commercially available 2-methylfuran. Yield of the example compound (III-11) was 55%, yield of the example compound (III-11)→(II-11) was quantitative, yield of the example compound (II-11)→(I-11) was 82%, and yield of the example compound (I-11)→(I-10) was 85%. Melting point of the example compound (I-10) was 201 to 202° C. NMR data are as follows.

NMR (CDCl$_3$, 300 MHz); δ (ppm) 2.45 (3 H, s), 5.18 (1 H, brs), 6.88 (2 H, d, J=7.6), 7.11 (2 H, t. like), 7.1–7.3 (4 H, m), 7.35 (1 H, d, J=7.6), 7.45 (2 H, m)

Thus, as has been described in the foregoing, the production method of the invention has rendered possible mass production of various tribenzazepine compounds. As a result, it rendered possible simple and easy production of a new electric charge transportation agent having tribenzazepine structure in its molecule, which is promising as a material for use it the electrophotographic photosensitive materials or organic electroluminescence (EL) devices, and its practical possibility therefore was increased.

The entire disclosure of each and every foreign patent application from which the benefit of foreign priority has been claimed in the present application is incorporated herein by reference, as if fully set forth.

What is claimed is:

1. A method for producing a tribenzazepine compound represented by formula (I), which comprises dehydrating a compound represented by formula (II) to produce a compound represented by formula (1):

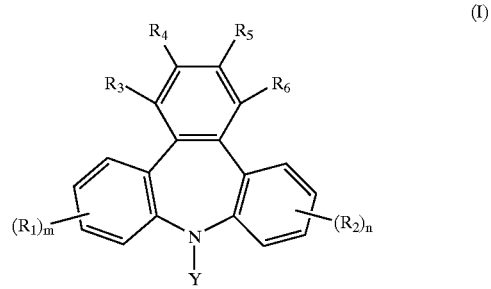

wherein Y represent s a hydrogen atom or an alkyl, aryl, acyl, alkoxycarbonyl, aryloxycarbonyl, alkanesulfonyl or arenesulfonyl group; R$_1$ and R$_2$ each represents a hydrogen or halogen atom or an alkyl, aryl, hydroxy, alkoxy, aryloxy, acyl, alkoxycarbonyl, aryloxycarbonyl, formyl, carboxyl, sulfo, nitro or amino group; R$_3$, R$_4$, R$_5$ and R$_6$ each represents a hydrogen atom or an alkyl or aryl group; and m and n each is an integer of from 1 to 4,

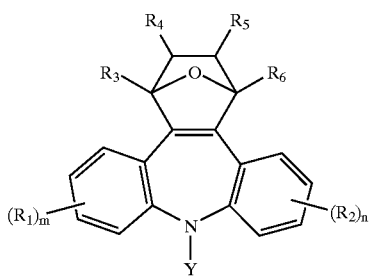

(II)

wherein Y, $R_1$, $R_2$, $R_3$, $R_4$, $R_5$, $R_6$, m and n are the same as those in formula (I).

2. A tribenzazepine compound represented by formula (IV):

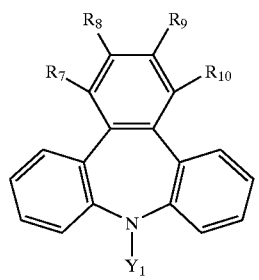

(IV)

wherein $Y_1$ represents a hydrogen atom or an alkyl, aryl, acyl, alkoxycarbonyl, aryloxycarbonyl, alkanesulfonyl or arenesulfonyl group; and $R_7$, $R_8$, $R_9$, and $R_{10}$ each represents a hydrogen atom or an alkyl group having 10 or less of carbon atoms, with that proviso that all of $R_7$ to $R_{10}$ are not hydrogen atoms at the same time and that $Y_1$ does not represent a hydrogen atom or an aryl group when $R_8$ is a methyl group and each of $R_7$, $R_9$ and $R_{10}$ is a hydrogen atom.

3. The method of claim 1, wherein the dehydration is carried out by heating in the presence of an acid catalyst.

4. The method of claim 3, wherein the acid catalyst is sulfuric acid, phosphoric acid, alkanesulfonic acid, arenesulfonic acid, Lewis acid, activated clay or solid acid.

5. The method of claim 3, wherein the temperature of the dehydration is from 50 to 200° C.

6. The method of claim 3, wherein the amount of acid catalyst is from 0.1 to 2 equivalents based on the compound of formula (II).

7. A method for producing a compound represented by formula (I), which comprises the following steps:

reducing a compound represented by formula (III) to produce a compound represented by formula (II); and
dehydrating the compound represented by formula (II) to produce the compound represented by formula (I):

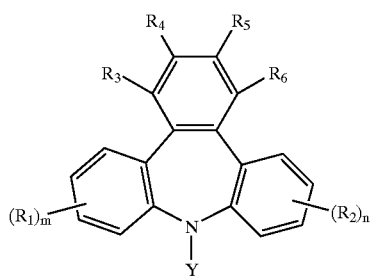

(I)

wherein Y represents a hydrogen atom or an alkyl, aryl, acyl, alkoxycarbonyl, aryloxycarbonyl, alkanesulfonyl or arenesulfonyl group; $R_1$ and $R_2$ each represents a hydrogen or halogen atom or an alkyl, aryl, hydroxy, alkoxy, aryloxy, acyl, alkoxycarbonyl, aryloxycarbonyl, formyl, carboxyl, sulfo, nitro or amino group; $R_3$, $R_4$, $R_5$ and $R_6$ each represents a hydrogen atom or an alkyl or aryl group; and m and n each is an integer of from 1 to 4

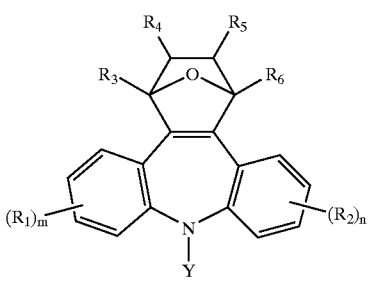

(II)

wherein Y, $R_1$, $R_2$, $R_3$, $R_4$, $R_5$, $R_6$, m and n are the same as those in formula (I)

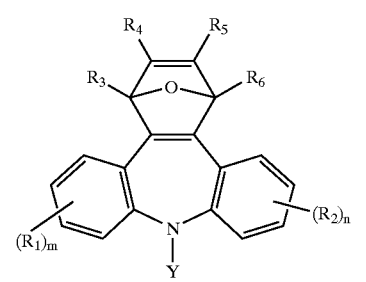

(III)

wherein Y, $R_1$, $R_2$, $R_3$, $R_4$, $R_5$, $R_6$, m and n are the same as those in formula (II).

8. The method of claim 7, wherein the reduction is carried out by using hydrogen and a catalyst.

9. The method of claim 7, wherein the reduction is carried out by a diimide reduction.

10. The method of claim 7, wherein the temperature of the reduction is from −20 to 100° C.

11. The method of claim 8, wherein the catalyst is a Raney nickel, palladium-carbon, or chlorotris(triphenylphosphine) rhodium(I).

12. The method of claim 8, wherein the amount of the catalyst is from 0.001 to 20 mol % based on the compound of formula (III).

13. The method of claim 12, wherein the amount of the diimide is from 1 to 10 equivalents based on the compound of formula (III).

14. The method of claim 7, wherein the dehydration is carried out by heating in the presence of an acid catalyst.

15. The method of claim 14, wherein the acid catalyst is sulfuric acid, phosphoric acid, alkanesulfonic acid, arenesulfonic acid, Lewis acid, activated clay or solid acid.

16. The method of claim 14, wherein the temperature of the dehydration is from 50 to 200° C.

17. The method of claim 10, wherein the amount of acid catalyst is from 0.1 to 2 equivalents based on the compound of formula (II).

* * * * *